United States Patent [19]

Giacobbe et al.

[11] 4,401,623

[45] Aug. 30, 1983

[54] USE OF CALCIUM CHLORIDE TO MINIMIZE HYDROFLUORIC ACID CORROSION TO GLASS DURING THE CHLORINATION OF 4-CHLOROBENZOTRIFLUORIDE

[75] Inventors: Thomas J. Giacobbe, Skillman; Grace Tsien, Colonia, both of N.J.

[73] Assignee: Rhone-Poulenc Agrochimie, Lyons, France

[21] Appl. No.: 284,303

[22] Filed: Jul. 17, 1981

[51] Int. Cl.³ .......................................... C23F 11/18
[52] U.S. Cl. .................................. 422/1; 106/14.21; 252/387; 252/389 R; 252/79.3; 422/7; 422/12
[58] Field of Search ................. 252/387, 389 R, 79.3; 106/14.21; 422/1, 7, 12

[56] References Cited

U.S. PATENT DOCUMENTS

| | | | |
|---|---|---|---|
| 3,932,130 | 1/1976 | Bennett et al. | 422/12 |
| 3,992,313 | 11/1976 | Anderson et al. | 252/392 |
| 4,138,355 | 2/1979 | Ferstandig | 422/12 |
| 4,293,376 | 10/1981 | Weingand | 252/79.3 |

OTHER PUBLICATIONS

Hudlicky, M.: "Chemistry of Organic Fluorine Compounds", 2nd Edition, John Wiley & Sons, N.Y., 1976, pp. 255–278.

Primary Examiner—Irwin Gluck
Attorney, Agent, or Firm—Morgan, Finnegan, Pine, Foley & Lee

[57] ABSTRACT

There is provided a method for preventing corrosion in a glass-lined vessel due to HF liberated from an organic liquid medium. The method involves adding $CaCl_2$ particles to this medium. This method is particularly useful in the chlorination of 4-chlorobenzotrifluoride to 3,4-dichlorobenzotrifluoride.

7 Claims, 3 Drawing Figures

CORROSION TO BOROSILICATE GLASS VS. TEMPERATURE WITH AND WITHOUT $CaCl_2$ PRESENT DURING THE CHLORINATION OF 4-CHLOROBENZOTRIFLUORIDE $CaCl_2$ PARTICLE SIZE EFFECT ON CORROSION (CHLORINATION AT 60°C)

USE OF CALCIUM CHLORIDE TO MINIMIZE HYDROFLUORIC ACID CORROSION TO GLASS DURING THE CHLORINATION OF 4-CHLOROBENZOTRIFLUORIDE

BACKGROUND OF THE INVENTION

Sodium 5-[2-chloro-4-(trifluoromethyl)phenoxy]-2-nitrobenzoate is a known herbicide which is presently in commercial use and is being produced in large quantities. This herbicidal compound is the sodium salt of the acid produced from the nitration of

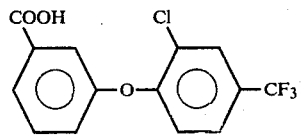

3-[2-chloro-4-(trifluoromethyl)]phenoxybenzoic acid which, in turn, may be produced by the oxidation of

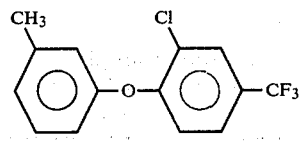

3-[2-chloro-4-)trifluoromethyl)]toluene which, in turn, may be produced by the coupling reaction of

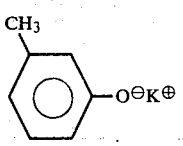

potassium 3-methylphenate with

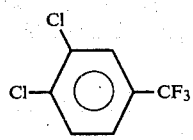

The compound 3,4-dichlorobenzotrifluoride may, in turn, be produced from the chlorination of

4-chlorobenzotrifluoride (p-CBTF)

During the chlorination of 4-chlorobenzotrifluoride to 3,4-dichlorobenzotrifluoride it has been found that a small amount of hydrogen fluoride is generated which poses a severe corrosion-to-glass problem. Since this chlorination reaction is generally conducted in a glass-lined vessel it was mandatory that this corrosion be minimized.

SUMMARY OF THE INVENTION

This invention provides a method for preventing corrosion in a glass-lined vessel due to the presence of HF liberated from an organic liquid medium within said vessel, said method comprising adding to said medium a corrosion preventing amount of particles of $CaCl_2$.

DETAILED DESCRIPTION

The presumed source of the HF in this chlorination is hydrolysis of partially fluorinated compounds present in the starting material. This hypothesis is supported by the presence of 4-chlorobenzodifluoride monochloride in the starting material, its gradual disappearance during the course of the reaction, and isolation and characterization of 3,4-dichlorobenzoic acid. Furthermore, the literature teaches that mixed chlorofluoromethanes hydrolyze with strong acid and this hydrolysis is catalyzed by iron and other metals. (Hudlicky M.: "Chemistry of Organic Fluorine Compounds", 2nd Edition, John Wiley & Sons, N. Y. 1976, P. 225-278.)

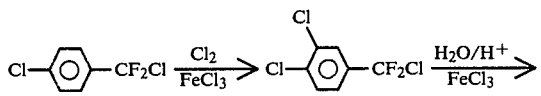

proven to be present in starting material.

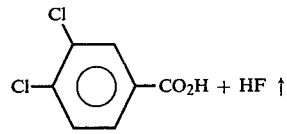

isolated and identified by-product.

Figure 1:
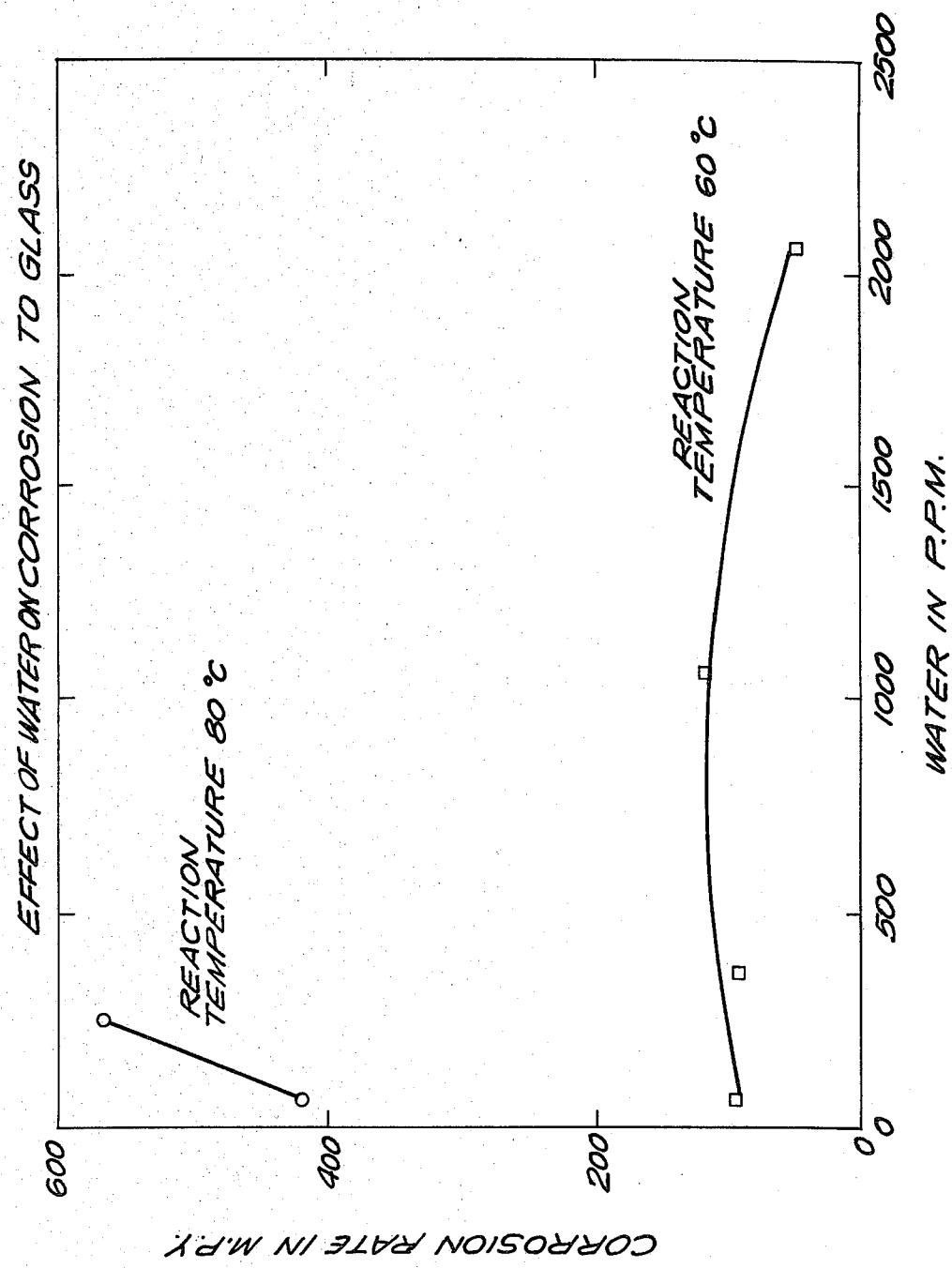
FIG. 1 is a line graph showing the effect of water in the liquid chlorination medium on the corrosion to glass.

As shown in FIG. 1, the corrosion rate increases with an increasing water concentration in the reaction mixture held at 80° C. This was expected since water is a reactant in the side reaction. However, this same effect was not observed at 60° C. The main sources of water for the hydrolysis, which results in HF formation, appear to be the water (~35 ppm) present in commercially available chlorine and the water contained in the 4-chlorobenzotrifluoride (~68 ppm).

Figure 2:
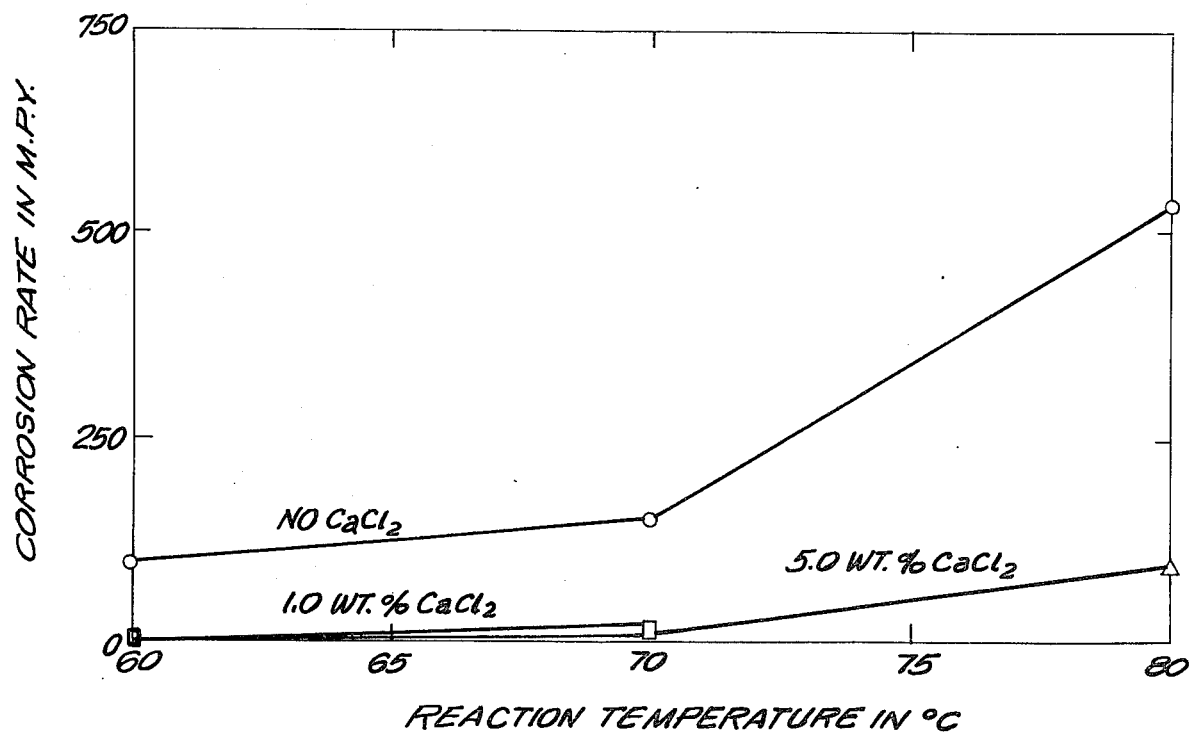
FIG. 2 is a line graph showing the effect of the temperature of the liquid chlorination medium on the corrosion to glass.

As shown in FIG. 2, the corrosion rate increases exponentially with the increase in reaction temperature. A reaction temperature of 80° C. was chosen previously by the scoping experiments to maximize both the reaction rate and the selectively to 3,4-dichlorobenzotrifluoride with ≦5% heavies. In view of this temperature dependence, a reaction temperature of 60° C. is preferred in order to minimize the corrosion rate while still allowing the reaction to proceed in a reasonable time, e.g., 4.5 hrs.

Figure 3:
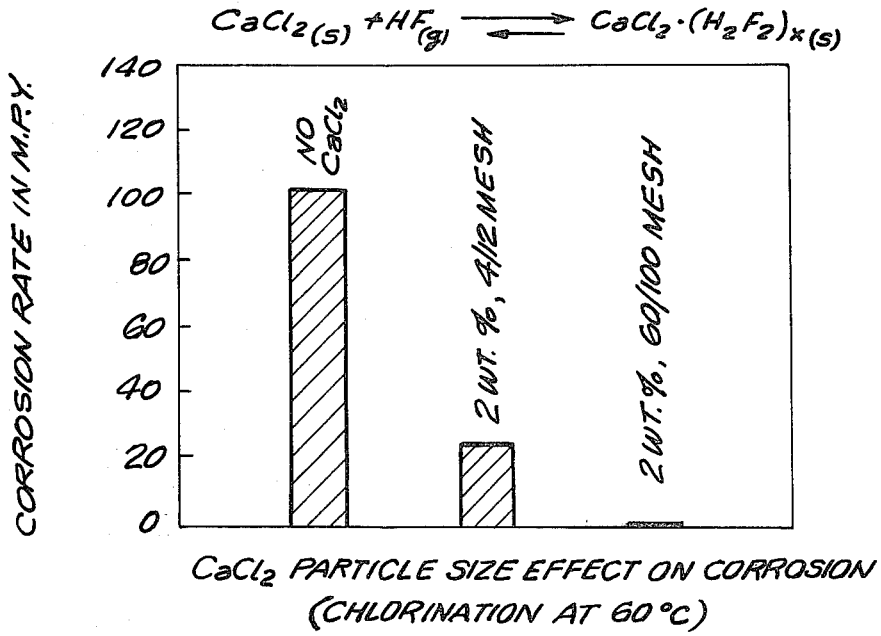
FIG. 3 is a bar graph showing the effect of $CaCl_2$ particle size in the liquid chlorination medium on the corrosion to glass.

While not wishing to be limited by any particular mode of action or theory, calcium chloride presumably reacts with HF to form a hydrated-type complex $[CaCl_2.(H_2F_2)_x]$. Since $CaCl_2$ is not soluble in the organic phase, the absorption of HF by $CaCl_2$ occurs mainly at the solid-liquid interphase. Therefore, good agitation and small particles of $CaCl_2$ were found to be essential for optimal removal of the HF. At a reaction temperature of 60° C., the corrosion rate was reduced to nil by adding 1 wt %, 60/100 mesh $CaCl_2$ based on the weight of 4-chlorobenzotrifluoride in the well agitated mixture (FIG. 2). However, as shown in FIG. 3, a corrosion rate of 21.7 m.p.y, was observed when the $CaCl_2$ particles were larger, 4/12 mesh.

In view of the above disclosure, it is preferred to add about 2 wt %, 60/100 mesh $CaCl_2$, based upon the weight of 4-chlorobenzotrifluoride into the reaction mixture to protect the glass from corrosion during the chlorination reaction at 60° C. Since this absorption reaction is reversible after the chlorination reaction, the solid $CaCl_2$-containing complex $[CaCl_2 \cdot (H_2F_2)_x]$ should be removed from the system. It is noted that metal surfaces may catalyze HF generation. Thus, presence of metals in the glass-lined chlorination reactor should be avoided.

GENERAL PROCEDURE FOR DETERMINING CORROSION RATE TO GLASS DURING THE CHLORINATION OF 4-CHLOROBENZOTRIFLUORIDE

A standard laboratory chlorination of 4-chlorobenzotrifluoride (p-CBTF) was made by bubbling the chlorine gas at a rate of 19 g $Cl_2$/100 g p-CBTF/hr through a charge of 1.0 g $FeCl_3$/100.0 g p-CBTF and 2.0 g $CaCl_2$ (60/100 mesh) 100 g p-CBTF in a 250 ml 3-neck glass flask. Agitation was via magnetic stir bar. A temperature of 60° C. is maintained using a heat lamp connected to a variac, and the temperature was measured with a thermometer placed in the reaction mixture.

The chlorine flowed from a cylinder through a regulator, a rotometer meter, a glass check valve, and finally through a fritted glass sparge tube into the reaction mixture. The off-gas passed through a condenser to a scrubber containing 16% NaOH.

Excess moisture was kept from the reaction by keeping the $FeCl_3$, $CaCl_2$ and all equipment needed for transferring these to the flask in a glove bag with a $N_2$ atmosphere.

A new flask which had been cleaned with concentrated HCl, washed and dried, was kept in a constant temperature and humidity atmosphere where it was weighed to the nearest 0.1 mg. This eliminated the effect of day to day climate changes on weighings. The flask was then placed, unstoppered, in the $N_2$ filled glove bag to dry.

The $CaCl_2$ and $FeCl_2$ were transferred to the flask while in the glove bag. The flask was stoppered and removed from the glove bag. The p-CBTF was weighed and quickly poured into the flask. The thermometer, sparge tube, and condenser were placed on the flask, and the mixture was agitated for 30 minutes prior to heating.

The $Cl_2$ addition was started when the reaction temperature reaches 50° C. The reaction is slightly exothermic and must be watched constantly for the first 30 minutes. Once the reaction was stabilized it was checked every 15 minutes to make sure the temperature and $Cl_2$ flow were correct.

Samples were taken periodically and analyzed on the G.C. The $Cl_2$ addition and heat was stopped when the G.C. showed the area % of p-CBTF toe be ~27% (73% conversion). Additional chlorination was observed while the reaction cooled. The goal was to obtain 7% conversion of p-CBTF.

The material was then removed from the flask and the flask thoroughly cleaned as before and replaced in the constant temperature and humidity atmosphere overnight prior to wedging.

The amount of corrosion was calculated as follows:

$$\text{Corrosion rate } (m.p.y.) = \frac{(\text{wt. loss mg}) (534)}{(\text{area, in}^2) (\text{time, hr}) (\text{material density, g/cc.})}$$

Where the area of 250 ml 3-neck glass flask is calculated as follows:

$$\text{Area} = 4\pi \left( \sqrt[3]{\frac{3}{4} \frac{V}{\pi}} \right)^2$$

$$= 4\pi \left( \sqrt[3]{\frac{3}{4\pi} \frac{250}{16.39}} \right)^2$$

$$= 29.7409 \text{ in}^2$$

with the density of borosilicate glass taken as 2.20 g/cc.
Test results are set forth in Tables I, II, III and IV.

TABLE I
EFFECT OF $H_2O$ ON CORROSION TO GLASS DURING CHLORINATION REACTION

| $H_2O$ Conc. (ppm) | Reaction Temp | RXN Time (>75% conv.) | Wt. Loss in Flask (grams) | Calcd. Corrosion rate (m.p.y.) |
|---|---|---|---|---|
| 85 | 80° C. | 3 hr | 0.1546 | 420 |
| 256 | 80° C. | 3 hr | 0.208 | 565.2 |
| 68 | 60° C. | 4.5 hr | 0.0556 | 101 |
| 368 | 60° C. | 4.5 hr | 0.0527 | 95.5 |
| 1068 | 60° C. | 4.5 hr | 0.0673 | 121.9 |

TABLE II
EFFECT OF TEMPERATURE ON CORROSION TO GLASS DURING CHLORINATION REACTION

| Temp (°C.) | RXN Time (>75% conv.) | Wt. Loss in Flask (gram) | Corrosion Rate (m.p.y.) |
|---|---|---|---|
| 60 | 4.5 hr | 0.0556 | 101 |
| 70 | 4 hr | 0.0730 | 148.8 |
| 80 | 3 hr | 0.1970 | 535 |

TABLE III
EFFECT OF CALCIUM CHLORIDE ON CORROSION TO GLASS DURING CHLORINATION REACTION

| $CaCl_2$ Conc. (60/100 Mesh) | RXN Temp. (°C.) | RXN Time (>75% Conv.) | Wt. Loss in Flask (gram) | Corrosion Rate (m.p.y.) |
|---|---|---|---|---|
| 1 wt % | 60 | 4.5 hr | 0 | 0 |
| 2 wt % | 60 | 4.5 hr | 0 | 0 |
| 1 wt % | 70 | 4 hr | 0.0128 | 26 |
| 5 wt % | 80 | 3 hr | 0.0368 | 100 |

TABLE IV
EFFECT OF CALCIUM CHLORIDE PARTICLE SIZE ON CORROSION RATE AT 60° C.

| Particle Size | $CaCl_2$ Conc. | Run Time (>75% Conv.) | Wt. Loss in Flask | Corrosion Rate (m.p.y.) |
|---|---|---|---|---|
| — | — | 4.5 hr. | 0.0556 | 100 |
| 4/12 mesh | 2 wt % | 4.5 hr | 0.0113 | 21.7 |

TABLE IV-continued

| | | EFFECT OF CALCIUM CHLORIDE PARTICLE SIZE ON CORROSION RATE AT 60° C. | | | |
|---|---|---|---|---|---|
| Particle Size | CaCl$_2$ Conc. | Run Time (>75% Conv.) | Wt. Loss in Flask | Corrosion Rate (m.p.y.) | |
| 60/100 mesh | 2 wt % | 4.5 hr | 0 | 0.0 | |

What is claimed is:

1. A method for preventing corrosion in a glass-liquid vessel due to the presence of HF liberated from an organic liquid medium within said vessel, said method comprising adding to said medium a corrosion preventing amount of particles of CaCl$_2$.

2. A method according to claim 1, wherein said HF is liberated during the chlorination of 4-chlorobenzotrifluoride to 3,4-dichlorobenzotrifluoride, said chlorination taking place in said organic liquid medium.

3. A method according to claim 1, wherein said organic liquid medium is agitated.

4. A method according to claim 1, wherein said CaCl$_2$ particles are 60 mesh size or smaller.

5. A method according to claim 4, wherein said CaCl$_2$ particles are 60/100 mesh size.

6. A method according to claim 2, wherein said chlorination takes place at about 60° C.

7. A method according to claim 6, wherein said CaCl$_2$ particles are 60/100 mesh size and said particles are present in said organic liquid medium in an amount of about 2 wt %, based upon the weight of 4-chlorobenzotrifluoride at the start of the chlorination.

* * * * *

UNITED STATES PATENT AND TRADEMARK OFFICE
CERTIFICATE OF CORRECTION

PATENT NO. : 4,401,623
DATED : August 30, 1983
INVENTOR(S) : Thomas J. Giacobbe and Grace Tsien It is certified that error appears in the above-identified patent and that said Letters Patent is hereby corrected as shown below:

At column 5, line 10 "liquid" should read -- lined--.

Signed and Sealed this

Twenty-fifth Day of October 1983

[SEAL]

Attest:

Attesting Officer

GERALD J. MOSSINGHOFF

Commissioner of Patents and Trademarks